(12) United States Patent
Wood

(10) Patent No.: US 9,089,463 B1
(45) Date of Patent: Jul. 28, 2015

(54) PATIENT HEAD SUPPORT FOR RECEIVING MEDICAL TREATMENT IN THE PRONE POSITION

(71) Applicant: Thomas Wood, Page, AZ (US)

(72) Inventor: Thomas Wood, Page, AZ (US)

( * ) Notice: Subject to any disclaimer, the term of this patent is extended or adjusted under 35 U.S.C. 154(b) by 0 days.

(21) Appl. No.: 14/337,343

(22) Filed: Jul. 22, 2014

Related U.S. Application Data

(60) Provisional application No. 61/856,902, filed on Jul. 22, 2013.

(51) Int. Cl.
*A61G 7/07* (2006.01)
*A61M 16/06* (2006.01)
*A61M 16/00* (2006.01)
*A61M 16/08* (2006.01)

(52) U.S. Cl.
CPC ............ *A61G 7/072* (2013.01); *A61M 16/0057* (2013.01); *A61M 16/06* (2013.01); *A61M 16/0875* (2013.01)

(58) Field of Classification Search
CPC ........................................................ A61G 7/07
USPC ............................................. 5/636–639, 622
See application file for complete search history.

(56) References Cited

U.S. PATENT DOCUMENTS

D456,516 S * 4/2002 Cheshaek et al. ............ D24/183
2009/0133698 A1* 5/2009 Kuhlmann ............... 128/205.25

* cited by examiner

*Primary Examiner* — Fredrick Conley

(57) ABSTRACT

A patient head support for treatment in the prone position. A patient head support apparatus which facilitates management of the respiratory function of a patient residing in a prone position. The apparatus includes a support base and a deformable resilient insert placed within it. The insert has a depression for receiving the patient's face either with or without a facial mask. The apparatus is provided with a passageway for delivery of gaseous inhalant to the patient and a coupling means at the external port to facilitate connection of the tubing to an external supply of an inhalant gas, allowing patients to be sedated rather than anesthetized for treatment.

6 Claims, 3 Drawing Sheets

PATIENT HEAD SUPPORT FOR RECEIVING MEDICAL TREATMENT IN THE PRONE POSITION

CROSS-REFERENCE TO RELATED APPLICATION

This application claims the benefit of U.S. Provisional Patent Application No. 61/856,902 filed Jul. 22, 2013, the contents of which are hereby incorporated by reference.

TECHNICAL FIELD

This invention relates to a head support for a patient undergoing a surgical procedure in a prone position while aiding the ventilating and monitoring of respiratory function of the patient.

BACKGROUND

The conventional practice of administering a gaseous anesthetic to a patient about to receive a minor surgical treatment has generally included the placement of a breathing tube in the supine patient prior to manipulating the patient into a face-down, or prone position. This procedure has been adopted to avoid relinquishing control of the airway of an anesthetized patient. As a result, certain types of operations performed on the backside of a patient have typically used a general anesthetic with insertion of a breathing tube prior to rotating the patient to the prone position. At the conclusion of the surgical procedure, the patient is returned to the supine position. The manipulation of the anesthetized patient without his cooperation is not easy for any patient and cannot be accomplished by one person.

A substantial number of operations are performed with the patient in the prone position. If many of these operations can be performed without the use of a general anesthetic, the breathing tube and the need to change the positions of an anesthetized patient can be substantially reduced, as is the amount of time required for the procedure and for use of the operating room. Furthermore, the elimination of the combination of general anesthetic and breathing tube enables the reflexes of the patient to be maintained during the procedure. The patient under sedation rather than general anesthetic manages his own airway. In both cases, a standard facial mask is used to convey oxygen, provide ventilation, and permit monitoring of the respiratory function of a patient.

While the advantages of sedation to permit a cooperating patient to assume a prone position when undergoing certain types of procedures are recognized, the lack of suitable head supporting apparatus that can accommodate a patient wearing a facial mask in a face-downward position has prevented the adoption of this procedure. Among the problems confronting the staff planning to operate with a prone-positioned patient is the importance of maintaining clearance between the face mask and the patient so as to ensure continuous flow of gaseous inhalant and to provide a volumetric region which can receive and retain any emissions from the patient without impeding the flow of gaseous inhalant. In addition, the inhaled gases are supplied through tubing, which must remain free from pressure points, such as snarls, kinks, and any contact pressure from adjacent structural members.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

A patient head support for treatment in the prone position. A patient head support apparatus which facilitates management of the respiratory function of a patient residing in a prone position. The apparatus includes a support base and a deformable resilient insert placed within it. The insert has a depression for receiving the patient's face either with or without a facial mask. The apparatus is provided with a passageway for delivery of gaseous inhalant to the patient and a coupling means at the external port to facilitate connection of the tubing to an external supply of an inhalant gas, allowing patients to be sedated rather than anesthetized for treatment.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

Figure 1:
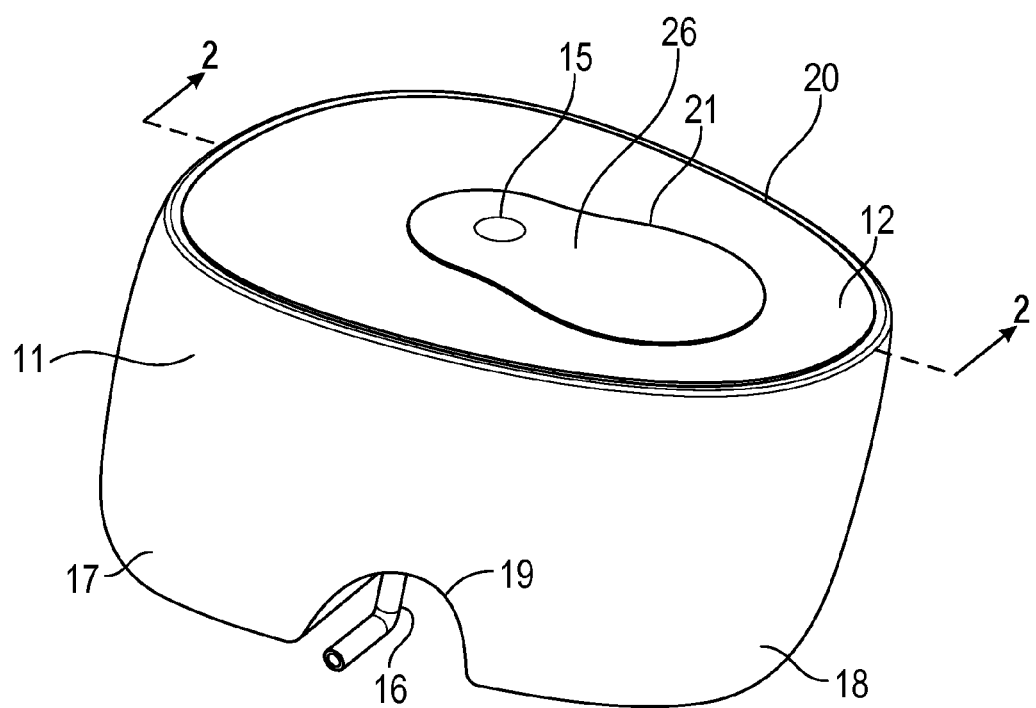
FIG. 1 is a view in perspective of one example of the invention.

The detailed description provided below in connection with the appended drawings is intended as a description of the present examples and is not intended to represent the only forms in which the present examples may be constructed or utilized. The description sets forth the functions of the examples and the sequence of steps for constructing and operating the examples. However, the same or equivalent functions and sequences may be accomplished by different examples.

Among the objectives of the present invention is the provision of apparatus for enabling patients about to undergo an operation on the backside of the torso to assume a prone position prior to sedation and to maintain the prone position during the procedure while utilizing a face mask for the ventilation, oxygen supply, and monitoring functions required during the operation. The invention provides support for the facial area of the patient in the regions surrounding the area covered by the facial mask so as to enable continuous flow of gaseous inhalant to and from the patient. The absence of a breathing tube results in the sedated patient controlling his own airway, since the reflex action is maintained in force and effect. The use of the subject invention reduces the time required for use of the surgical facilities, eliminates the need to manipulate and position a non-cooperating patient, as well as avoiding the effects of general anesthesia and a breathing tube on the patient.

The present invention is directed to an apparatus which facilitates the management of the respiratory function of a patient residing in a prone position. The apparatus includes a support base having a relatively large surface area top with a concavity located therein. The base has a centrally-located channel extending from the concavity to an external port. The support base is placed in an appropriate position on a stable surface to receive the head of the patient.

A deformable resilient insert is placed within the concavity in the support base. The insert has a depression therein for receiving the face of the patient. The resilient insert is preferably removable from the base so that different sized depressions may be used based on the age or facial characteristics of the patient. The insert is provided with a passageway, which is used for delivery of gaseous inhalant from the channel in the support base to the patient.

Flexible tubing extends from the external port on the support base, through the channel in the support base and is fed through the passageway in the resilient insert, and ultimately connected to a facial mask. The tubing is provided with a coupling means at the external port to facilitate connection of the tubing to an external supply of an inhalant gas and a means for attaching to a port on the facial mask.

In operation, the support base of the present invention has sufficient rigidity to support the weight of the patient's head without substantial deformation of the support base. As a result, the deformable resilient insert in the concavity in the top surface of the support base receives and distributes the weight of the patient's head around the central depression. The peripheral region of the resilient insert is deformed by the weight, but the depression permits the patient to wear a conventional facial mask without the facial mask undergoing significant. In a preferred example, the resilient insert has a lesser rigidity than the facial mask so that the resilient insert conforms to the mask. The resilient insert is preferably ovate to approximate the general facial shape of a patient and to more evenly distribute the weight of the patient's head throughout the resilient insert.

When the patient is equipped with a facial mask and positioned in the face-down, or prone position with the patient's face on the resilient insert, the one or more ports of the facial mask are connected to the external gas supplies via the flexible tubing extending upwardly through the support base and resilient insert to couple to the input port or ports on the facial mask. The patient, being sedated rather than anesthetized, is able to assume the appropriate position without major assistance while coupling of the tubing is effected. The patient retains control of his airway and the patient's own reflex action is available to maintain an open airway during the procedure. Any discharge from the patient will be received in the mask without impeding the flow of gaseous inhalant to the patient.

FIG. 1 is a view in perspective of one example of the invention. FIG. 1 shows a support base 11, a deformable resilient member 12, and a facial mask 26. The support base 11 is typically a molded article comprised of plastic. The molded plastic has sufficient rigidity such that it does not substantially change dimensions when supporting the patient's head in a face-down, or prone, position. The support base is usually placed on a surface at the location where the patient's head is to be positioned. The support base 11 is shown with spaced supporting legs 17 and 18. The legs are separated by a central cut-out section 19 through which a means for coupling 16 the present invention to external gas supplies extends.

The support base is provided with a concavity 20 in the upper surface wherein the deformable resilient member 12 resides. The deformable resilient insert member 12 is typically formed of an expanded plastic, such as polyurethane foam or the like, that has predictable deformation characteristics and is provided with a second concavity 21 in which the facial mask 26 resides. The facial mask 26 is a conventional facial mask, and is provided with one or more ports 15 for connection to external gas supplies.

Figure 2:
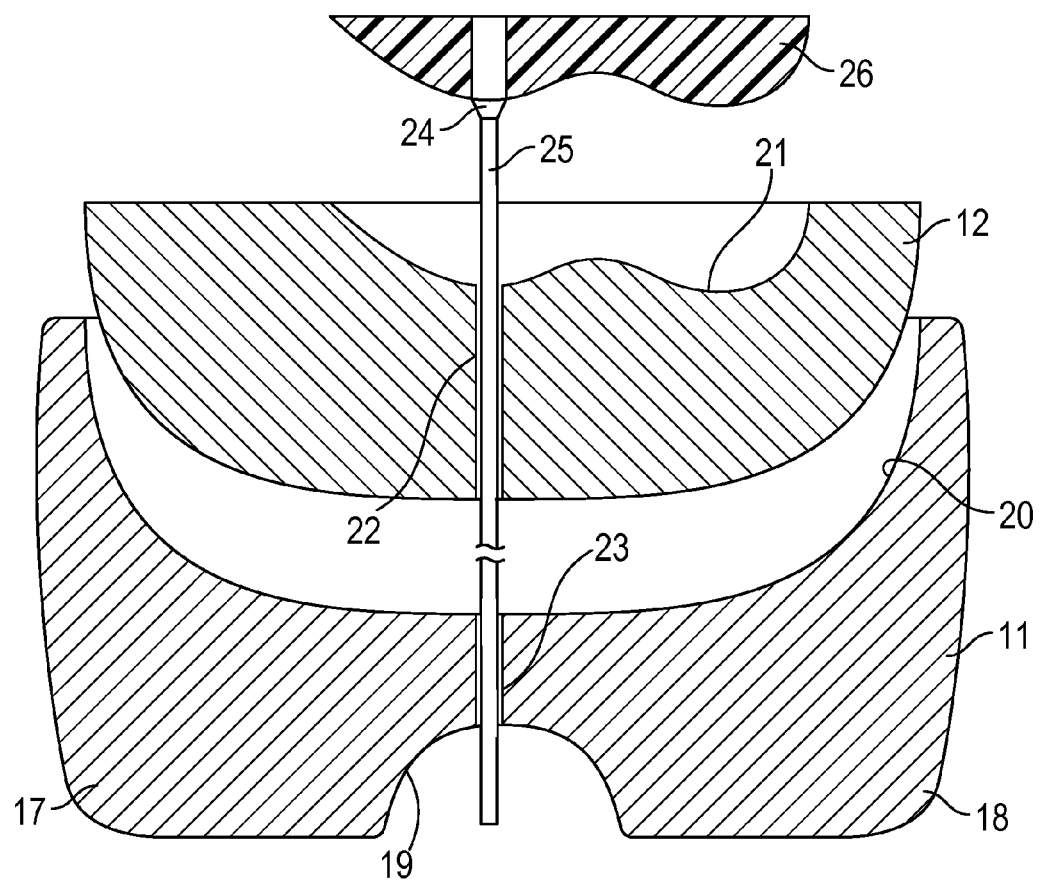
FIG. 2 is a cross section of the example of FIG. 1 taken along line 2-2.

FIG. 2 is a cross section of the example of FIG. 1 taken along line 2-2 in FIG. 1, and shows more clearly the relationship between the support base 11, the deformable resilient member 12, the flexible tubing for gas transport 25, and the facial mask 26. The concavity 20 in the support base 11 is shaped to receive the deformable resilient member 12. A deformable resilient insert member 12 is placed within the concavity 20 in the top surface of the support base. The insert 12 is removable from base 11. A depression 21 is formed in the top surface of the insert 12 and connects with a passageway 22, which extends vertically downward to a passage 23 formed in the base 11.

The depression 21, typically molded into the insert 12, is dimensioned to receive a facial mask 26 of the type normally used to supply oxygen or other inhalants to a patient. The means of attachment of the mask to the patient are not pertinent to the subject invention and detail is omitted from the facial mask 26 of FIG. 2. Since the size of the facial mask used varies based on the age, structure, and morphology of the patient, the resilient insert 12 can be replaced with other inserts having larger or smaller depressions 21 molded therein to fit the requirements of the facial mask utilized by the patient being served. The facial mask 26 has at least one port 24 therein to receive the flow of oxygen or other gas through a delivery tube 25, which is shown extending downwardly through passageway 22 within the deformable resilient insert 12, to channel 23 within the base 11. The delivery tube 25 is provided with a means for coupling (not shown) the delivery tube to an external supply of an inhalant gas at the central cutout 19 of the support base 11. Such a modular system advantageously provides for a universal support base 11 with interchangeable resilient inserts 12 that accommodate various sized facial masks.

Figure 3:
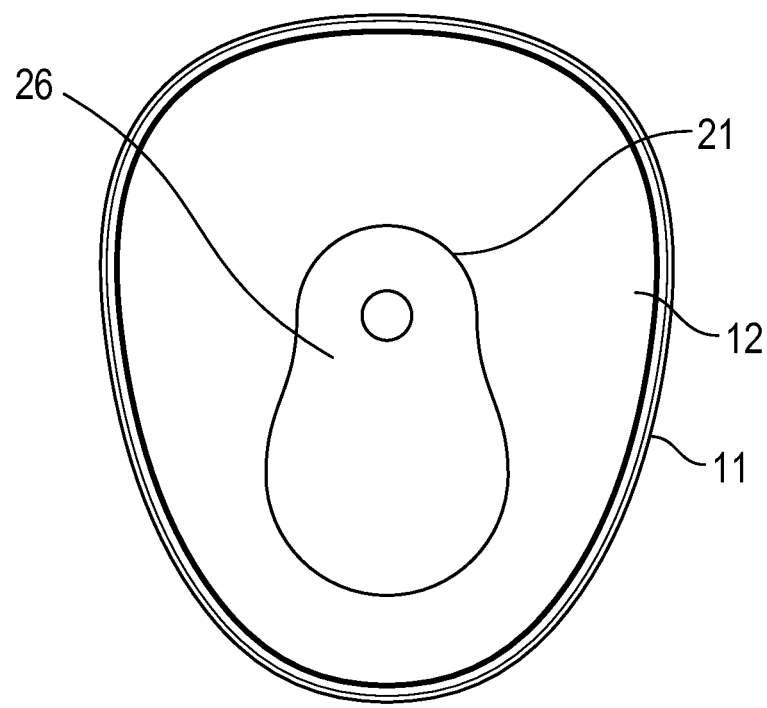
FIG. 3 is a top view of the example of FIG. 1.

FIG. 3 is a top view of the example of FIG. 1. The plan view of FIG. 3 shows the outline of the depression 20 formed in the base 11 to receive the deformable resilient insert 12, and the outline of the depression 21 formed in the resilient insert 12 to receive the facial mask 26. The preferred shape of the support base 11 is ovate, since this approximates the shape of a patient's facial structure. The depression 21 in insert 12 is ovate to sealingly engage about the edge of the facial mask 26, and provide a reservoir in the region beneath the mouth and nose. Thus, the broader region of the resilient deformable insert 12 receives the chin region of the face. The ovate shape of the base allows the weight of the patient's head to be more evenly distributed about the peripheral region of the resilient insert 12 so that the pressure thereof is shared and distortion of the resilient insert 12 is minimized.

In use, the support base 11 is located on a firm surface where the patient's head is to reside during the procedure. The resilient insert 12 is selected based on the size of the facial mask 26 the patient will receive. The delivery tube 25 is fed up through the centrally-located channel 23 into the passageway 22 and attached to the port 24 of the facial mask 26. The facial mask can be attached to the head of the patient by an elastic strap (not shown) or in some cases the pressure of the patient's head against the mask, which urges it into the depression 21 in the resilient insert 12, is sufficient to provide sealing engagement between patient and mask. If desired, a tacky surface could be provided on the; mask to prevent slippage. The patient is in the prone position and the delivery tube is coupled via connector 16 to the source of inhalant gas and monitoring equipment, as needed. The application of a sedative to the patient is sufficient for many minor operations and the need for a breathing tube is obviated.

While the foregoing description has referred to a preferred example of the invention, it is to be noted that modifications and variations may be made therein without departing from the scope of the invention. In particular, the deformable insert may be employed without the use of a face mask with the depression therein used to serve as the face mask. In this application, the contour of the depression takes into account the particular facial structure of the individual and multiple passages for inhalant gas are recommended.

The invention claimed is:

1. An apparatus for facilitating the management of the respiratory function of a patient residing in a prone position, the apparatus comprising;
   (a) an ovate support base having a first concavity located in a top surface thereof, and a substantially flat bottom surface thereof, the base having a centrally-located channel extending from the first concavity to an external port;
   (b) a deformable resilient insert selected from a plurality of available deformable inserts matching the first concavity and each having a second concavity of differing sizes dimensioned to be received in the first concavity of the support base, the insert having the second concavity forming a depression therein for receiving a patient's face therein and shaped to form a void to accommodate a face mask and forming a reservoir beneath the nose and mouth of the patient, the insert containing a passageway for delivery of gasses from the channel to the patient; and
   (c) a connector connecting the external port to a source of gasses whereby the gasses are transported through the resilient insert to the face of the patient whereby the ovate shape of the base allows a weight of the patient's head to be more evenly distributed about the peripheral region of the deformable resilient insert so that pressure is distributed and distortion of the deformable resilient insert is minimized.

2. An apparatus for facilitating the management of the respiratory function of a patient residing in a prone position, the apparatus comprising;
   (a) an ovate support base having sufficient rigidity to support the weight of a patient's head without substantial deformation, the support base having a first concavity in the top surface thereof and a substantially flat bottom surface thereof;
   (b) a deformable resilient insert selected from a plurality of available deformable inserts matching the first concavity and each having a second concavity of differing sizes and shaped to form a void to accommodate a face mask and forming a reservoir beneath the nose and mouth of the patient and dimensioned to be received in the first concavity, the insert having a depression in the top surface thereof to conformably receive a patient wearing facial mask of the type having at least one input port;
   (c) a delivery tube coupled to the input port of the facial mask and extending downwardly through the resilient insert and support base for connection to a source of an inhalant gas whereby the ovate shape of the base allows a weight of the patient's head to be more evenly distributed about the peripheral region of the deformable resilient insert so that pressure is distributed and distortion of the deformable resilient insert is minimized.

3. The apparatus of claim 2 wherein the depression in the top surface of the deformable resilient insert conformable receives a patient without a facial mask while maintaining a volume for inhalant gas.

4. The apparatus of claim 2 further comprising a facial mask for affixation to a patient, the mask having greater rigidity than the deformable resilient insert whereby the insert conforms to the mask upon contact therebetween.

5. The apparatus of claim 3 wherein the deformable resilient insert has an ovate depression formed therein.

6. The apparatus of claim 4 wherein the support base has an ovate concavity located in the top surface thereof.

* * * * *